(12) United States Patent
Voigt et al.

(10) Patent No.: US 7,609,370 B2
(45) Date of Patent: Oct. 27, 2009

(54) SINGLE DETECTOR BASED DUAL EXCITATION WAVELENGTH SPECTRA DISPLAY

(75) Inventors: Thomas Voigt, Export, PA (US); David Tuschel, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 85 days.

(21) Appl. No.: 12/017,409

(22) Filed: Jan. 22, 2008

(65) Prior Publication Data

US 2008/0212079 A1    Sep. 4, 2008

Related U.S. Application Data

(60) Provisional application No. 60/881,894, filed on Jan. 23, 2007.

(51) Int. Cl.
  *G01J 3/44* (2006.01)
  *G01J 3/443* (2006.01)
  *G01N 21/64* (2006.01)
  *G01N 21/65* (2006.01)
(52) U.S. Cl. .......................... 356/73; 356/301; 356/318; 356/328
(58) Field of Classification Search .................. 356/72, 356/73, 301, 318

See application file for complete search history.

(56) References Cited

U.S. PATENT DOCUMENTS

| 5,757,483 | A  | * | 5/1998 | Pierce, III | .................... 356/328 |
| 6,526,076 | B2 |   | 2/2003 | Cham et al. | |
| 6,717,133 | B2 |   | 4/2004 | Li | |
| 6,839,136 | B2 |   | 1/2005 | Mikes | |
| 7,397,561 | B2 | * | 7/2008 | Yoo | ........................... 356/328 |

* cited by examiner

*Primary Examiner*—F. L Evans
(74) *Attorney, Agent, or Firm*—Morgan Lewis & Bockius LLP

(57) ABSTRACT

A single detector based spectroscopy system using FAST (fiber array spectral translator) fibers and two excitation sources in conjunction with a holographic spectrum analyzer (HSA) to obtain simultaneous and selective display of spectroscopic regions of interest. A sample can be illuminated with different laser excitation wavelengths and resulting multiple spectra can be comparatively observed on a single display screen for more fruitful analysis of sample spectral responses (and, hence, sample chemical or physical properties) under different excitations. The HSA may be configured to focus on user-selected spectral regions of interest from different such spectra and a single CCD detector may be configured to collect spectral data from all selected spectral regions of interest in corresponding portions of the CCD pixel array, thereby allowing subsequent simultaneous display of such selected spectral regions of interest. The HSA may also allow simultaneous collection and display of portions of a single spectrum from a single excitation wavelength. A user can perform better comparative analysis when spectral regions of interest are juxtaposed with each other on a single electronic display.

28 Claims, 7 Drawing Sheets

SINGLE DETECTOR BASED DUAL EXCITATION WAVELENGTH SPECTRA DISPLAY

REFERENCE TO RELATED APPLICATION

The disclosure in the present application claims priority benefit under 35 U.S.C. §119(e) of the U.S. Provisional Application No. 60/881,894, titled "Dual Excitation Wavelength Spectra Display with Single CCD," and filed on Jan. 23, 2007, the disclosure of which is incorporated herein by reference in its entirety.

BACKGROUND

1. Field of the Disclosure

The present disclosure generally relates to spectroscopy systems and, more particularly, to a single detector based spectroscopy system employing dual illumination sources along with a configurable holographic spectrum analyzer for customizable simultaneous spectral displays.

2. Brief Description of Related Art

Modern spectroscopy systems rely on various optical properties of samples under investigation to elicit information about a sample's chemical and physical structure (e.g., chemical, molecular, or elemental composition), characteristics, and properties. A sample's spectrum may provide one or more of such information depending on the spectroscopy method employed for the investigation. Some examples of spectroscopy methods include Raman spectroscopy, infrared spectroscopy, fluorescence spectroscopy, mass spectrometry, x-ray diffractometry, etc. Each spectroscopy method may have a different level of specificity or discriminatory power. For example, a Raman spectrum generally has higher discriminatory power than a fluorescence spectrum and, hence, Raman spectroscopy is generally considered more specific for the identification of an unknown material. However, Raman scattered signals are typically far weaker than fluorescence emissions and, hence, Raman spectroscopy systems may require more sensitive signal collection optics and more selective data processing techniques to collect and process weaker Raman signals. Thus, pros and cons of various spectroscopy systems (e.g., cost, speed, accuracy, specificity, sensitivity, etc.) should be considered prior to selecting a spectroscopy approach for the application at hand.

FIG. 1 illustrates a prior art fiber array spectral translator (FAST) based spectroscopy system 10 that may be used for Raman spectroscopy. In the system 10, an object or sample 12 is shown to receive illumination from an illumination or excitation source 16 (e.g., a monochromatic illumination or laser illumination). Radiation reflected, emitted, or scattered from various illuminated regions in the sample 12 may be collected by collection unit 20 (e.g., a microscope objective) before the collected signal is fed to a two-dimensional (2D) array 22 of optical fibers as indicated by exemplary arrows 18 and 19 depicting optical signal propagation path from the sample 12 to the 2D fiber array 22. Three exemplary regions in the sample 12 are indicated by reference numerals 14A (cross-hatched circle), 14B (filled circle), and 14C (a circular ring). In the FAST system 10, one end of the fiber bundle (i.e., the end receiving optical signals from the collection unit 20) is shown formed in the shape of a 2D array of optical fibers 22, whereas the other end of the fiber bundle is shown arranged in a one-dimensional (1D) curvilinear array 24. Thus, the FAST system 10 may be considered to transform a 2D field of view (FOV) into a 1D arrangement at the entrance of a spectrometer slit 27 as shown in FIG. 1.

From the exemplary layout in FIG. 1, it is seen that each fiber in the 2D fiber bundle 22 may image a certain portion of the sample-as indicated by linking of three exemplary sample regions 14A-14C with corresponding fibers in the 2D fiber bundle-here, fibers numbered "21,""18," and "7," respectively in the exemplary set of thirty fibers (numbered from "1" through "30" in FIG. 1) in the 2D fiber bundle 22. The optical data set (i.e., photons reflected, emitted, or scattered from the illuminated sample 12) collected by all the thirty (30) fibers at the 2D end 22 is fed through the 1D curvilinear end 24 into the slit 27 of the spectrograph 26. The spectrograph 26 may be a holographic grating-based spectrometer, which may be coupled to an optical detector 28 (e.g., a charge coupled device or CCD) to store fiber-specific spectral information in the corresponding CCD rows as illustrated by three exemplary highlighted bars 14A-14C in a layout 30 of a CCD output array having an X-Y resolution of 1024×1024 pixels. In the layout 30, the reference numerals 14A-14C are used to indicate how correspondence is maintained among the similarly-numbered regions of interest in the sample 12, the corresponding fibers receiving optical data from these regions of interest (i.e., the fibers numbered "21," "18," and "7," respectively), and the CCD rows storing fiber-specific spectral information. Thus, a one-to-one correspondence between a CCD row and a sample region of interest may be achieved for spatially-resolved spectral data collection. Thus, as shown for example in FIG. 1, spectral information from the region 14A in the sample 12 may be collected by the fiber #21 (in the exemplary set of 30 fibers shown in FIG. 1) and may be stored as corresponding electrical charge in one of the rows in the CCD. Similarly, spectral content from other regions on the sample may also be stored in corresponding CCD rows to obtain a 2D image of the entire illuminated FOV (field of view) of the sample.

It is observed here that a third dimension for the 2D CCD layout 30 may be defined from the spectral information of the entire illuminated FOV of the sample 12. In the exemplary illustration in FIG. 1, each row in the CCD layout 30 is numbered from 1 through 30 to correspond with the total number of fibers in the FAST fiber bundle. Thus, it is understood that each CCD row represents a fiber-specific output from a fiber associated with that row, and that each fiber-specific output may contain a plurality of wavelengths that may be represented as various "columns" (not shown in the layout 30 in FIG. 1) in the CCD output 30. Hence, each CCD column can be redefined to a wavelength-specific 2D spatial image corresponding to the fiber bundle architecture and CCD storage mechanism. A plurality of such wavelength-specific 2D spatial images 32-1 through 32-n are illustrated in FIG. 1 as forming a hyperspectral image cube 34 formed from the spectral data stored in various CCD "columns" (along the X-axis), wherein, as noted before, each CCD column represents a wavelength-specific spatial (image) information collected by the FAST fibers and stored along the Y-axis. The third dimension (the Z-axis) may represent the individual wavelengths and can be defined by the spectral information of the CCD rows. This spectral information represents the material characteristic information of the illuminated FOV of the sample 12 as is known in the art. In the exemplary hyperspectral image cube 34 in FIG. 1, the mapping of spectral data from a sample region of interest across all wavelengths (along the Z-axis) is illustrated by dotted lines linking a spatial location of a region of interest (e.g., the region 14A) through all the spatial image frames 32-1 through 32-n.

It is noted here that all the figures herein are for illustrative purpose only; the figures are not drawn to scale and nor do they depict complete hardware or spectral details. Furthermore, the exemplary Raman spectra illustrated in various figures are depicted after appropriate removal of fluorescence and after baseline adjustments are carried out.

FIG. 2 depicts an exemplary Raman spectrum 40 collected from a sample 12 by one of the fibers in the FAST system 10 of FIG. 1. As discussed before, this spectrum may represent charge collected at one of the CCD rows corresponding to the fiber at issue. The entire CCD may thus contain spectral data from many such fibers—each CCD row may contain information to represent a similar Raman spectrum. Thus, in one embodiment, the spectrum 40 may represent an average of all Raman spectra collected by all FAST fibers in the system 10. As noted before, the fibers may collect light reflected, emitted, or scattered from the sample 12. Therefore, the actual spectral data content in the CCD rows may reflect fluorescence data as well as Raman data. The spectrum 40 in FIG. 2 is obtained after appropriate removal of the fluorescence portion and after the baseline adjustments are carried out. These procedures are not illustrated or discussed herein for the sake of brevity.

It is seen from FIG. 2 that a "typical" Raman spectrum 40 may include a fingerprint region 42, a C-H (carbon-hydrogen) stretch region 44, and a substantially less significant intervening region 46. It may be desirable to focus on or explore the fingerprint region 42 (which represents more information about chemical and physical characteristic of a sample under investigation), and sometimes the C-H stretch region 44 (which may provide information about carbon-hydrogen bonds in the sample material), in more detail in many spectroscopy applications. It may be further desirable to be able to have the fingerprint region 42 and the C-H stretch region 44 displayed simultaneously on a single display monitor or screen. For additional spectroscopic analysis, it may be also desirable to have simultaneous display of two user-selected spectral regions of interest, which may not necessarily include the fingerprint region 42 or the C-H stretch region 44.

In case of further spectroscopic exploration of chemical or physical properties of the sample 12, it may be desirable to devise a system containing multiple illumination sources so that the sample 12 can be illuminated with different laser excitation wavelengths and resulting multiple sample spectra can be comparatively observed for a more fruitful analysis of sample spectral responses (and, hence, sample properties) under different excitations. In such an event, it may be further desirable to be able to focus on selected spectral regions of interest from different such spectra and have a simultaneous display of such selected spectral regions of interest so as to enable a user to perform a better comparative analysis when spectra from different illumination sources are juxtaposed with each other on a single electronic display.

SUMMARY

In one embodiment, the present disclosure relates to a method that comprises illuminating a sample with first photons having a first excitation wavelength and collecting first spectral data from second photons reflected, scattered, or emitted from the sample when the sample is illuminated with the first photons. The first spectral data are collected using a first portion of an optical detector. The method also comprises illuminating the sample with third photons having a second excitation wavelength, wherein the second excitation wavelength is different from the first excitation wavelength. The method further comprises collecting second spectral data from fourth photons reflected, scattered, or emitted from the sample when the sample is illuminated with the third photons, wherein the second spectral data are collected using a second portion of the optical detector without removing the first spectral data collected by the first portion.

In a further embodiment, the present disclosure relates to a method that comprises displaying a first spectrum of a sample obtained when the sample is illuminated with first photons having a first excitation wavelength; displaying a second spectrum of the sample obtained when the sample is illuminated with second photons having a second excitation wavelength, wherein the second excitation wavelength is different from the first excitation wavelength; and allowing a user to select a first spectral region of the first spectrum and a second spectral region of the second spectrum. The method also comprises performing the following in response to selection of the first and the second spectral regions by the user: (i) illuminating the sample with the first photons; (ii) configuring a holographic spectrum analyzer to perform the following: receive a portion of third photons reflected, scattered, or emitted from the sample when the sample is illuminated with the first photons, and supply those of the third photons that are associated with only the first spectral region to a first portion of an optical detector; (iii) illuminating the sample with the second photons; and (iv) configuring the holographic spectrum analyzer to further perform the following: receive a portion of fourth photons reflected, scattered, or emitted from the sample when the sample is illuminated with the second photons, and supply those of the fourth photons that are associated with only the second spectral region to a second portion of the optical detector, wherein the first and the second portions of the optical detector are different, and wherein the first and the second portions together constitute the entire spectral data collection surface of the optical detector.

In an alternative embodiment, the present disclosure relates to a system that comprises a first illumination source for illuminating a sample with first photons having a first excitation wavelength; an optical detector having a first portion and a second portion that together constitute the entire spectral data collection surface of the optical detector, wherein the first portion is different from the second portion, and wherein the first portion of the optical detector is configured to collect first spectral data from second photons reflected, scattered, or emitted from the sample when the sample is illuminated with the first photons. The system also includes a second illumination source for illuminating the sample with third photons having a second excitation wavelength, wherein the second excitation wavelength is different from the first excitation wavelength; and the second portion of the optical detector that is configured to collect second spectral data from fourth photons reflected, scattered, or emitted from the sample when the sample is illuminated with the third photons, wherein the optical detector is configured to collect the second spectral data without removing the first spectral data collected by the first portion.

Thus, a single detector based spectroscopy system according to one embodiment of the present disclosure uses FAST (fiber array spectral translator) fibers and two excitation sources in conjunction with a holographic spectrum analyzer (HSA) to obtain simultaneous and selective display of spectroscopic regions of interest. A sample can be illuminated with different laser excitation wavelengths and resulting multiple spectra can be comparatively observed on a single display screen for more fruitful analysis of sample spectral responses (and, hence, sample chemical or physical properties) under different excitations. The HSA may be configured to focus on user-selected spectral regions of interest from different such spectra and a single CCD detector may be configured to collect spectral data from all selected spectral regions of interest in corresponding portions of the CCD pixel array, thereby allowing subsequent simultaneous display of such selected spectral regions of interest. The HSA may also allow simultaneous collection and display of portions of a single spectrum from a single excitation wavelength. A user can perform better comparative analysis when spectral regions of interest are juxtaposed with each other on a single electronic display.

BRIEF DESCRIPTION OF THE DRAWINGS

For the present disclosure to be easily understood and readily practiced, the present disclosure will now be described for purposes of illustration and not limitation, in connection with the following figures, wherein.

DETAILED DESCRIPTION

The accompanying figures and the description that follows set forth the present disclosure in embodiments of the present disclosure. However, it is contemplated that persons generally familiar with optics, operation and maintenance of optical instruments (including spectroscopic instruments), or optical spectroscopy will be able to apply the teachings of the present disclosure in other contexts by modification of certain details. Accordingly, the figures and description are not to be taken as restrictive of the scope of the present disclosure, but are to be understood as broad and general teachings. In the discussion herein, when any numerical range of values is referred or suggested, such range is understood to include each and every member and/or fraction between the stated range of minimum and maximum.

As noted before, present disclosure relates to a single detector based spectroscopy system employing dual illumination sources along with a configurable holographic spectrum analyzer for customizable simultaneous spectral displays. In spectroscopy applications involving more than one illumination source, the sample responses to different illumination wavelengths may not be identical. Hence, it may be desirable to selectively focus on portions of response spectra so as to compare, contrast, and further analyze sample responses to different excitation wavelengths. It is beneficial to a user of such spectroscopy system when user-selected portions of sample response spectra from two different illumination wavelengths are displayed simultaneously on a display screen. An exemplary utility of such selective focusing may be evident from the discussion of FIG. 3 hereinbelow.

Figure 3:
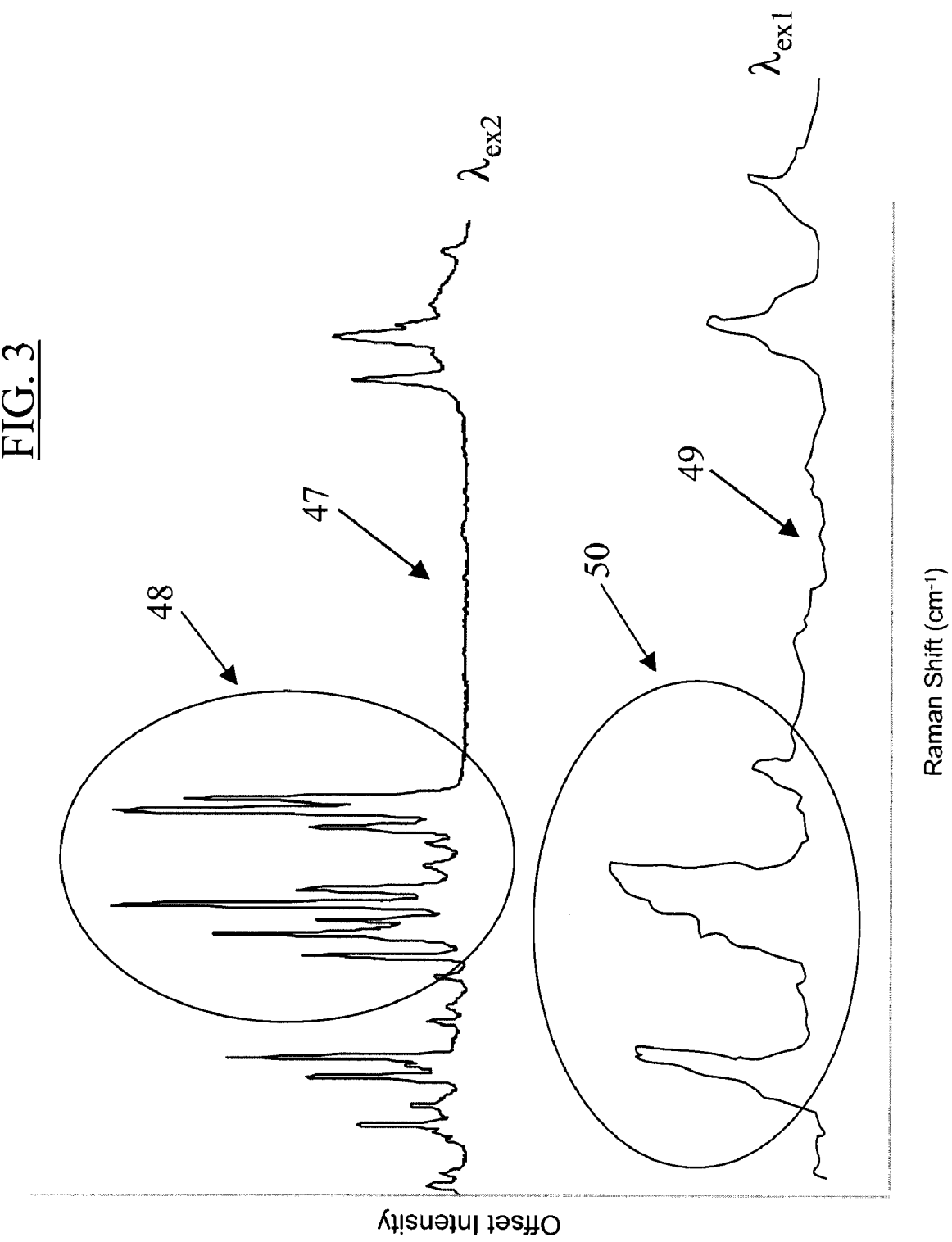
FIG. 3 illustrates two exemplary Raman spectra that may be obtained when a sample is illuminated with two different laser excitation wavelengths.

FIG. 3 illustrates two exemplary Raman spectra 47, 49 that may be obtained when a sample is illuminated with two different laser excitation wavelengths—$\lambda_{ex1}$ and $\lambda_{ex2}$. If the second excitation wavelength ($\lambda_{ex2}$) is higher than the first excitation wavelength ($\lambda_{ex1}$) (i.e., $\lambda_{ex2} > \lambda_{ex1}$), then the Raman spectrum 47 associated with the second excitation wavelength may have better resolution in the spectroscopic region of interest. For example, in the plots 47, 49 in FIG. 3, it is shown that the fingerprint region 48 from the higher excitation wavelength has better resolution (e.g., closely spaced peaks) than the corresponding fingerprint region 50 from the lower excitation wavelength. However, the spectrum 47 with better resolution may have lower free spectral range (FSR) (i.e., spectral separation between two consecutive passbands or spectral peaks) than the FSR in the spectrum 49 with lower resolution as can be observed from the spectral plots 47, 49 in FIG. 3. Thus, in spectroscopy analysis of fingerprint regions from spectra from two different excitation wavelengths, it may be desirable to have simultaneous displays of only regions 48 and 50 so as to be able to more closely analyze and compare spectral responses of the sample material to two different excitation wavelengths. Such analysis may lead to further information about chemical or physical properties of the sample under investigation.

Figure 1:
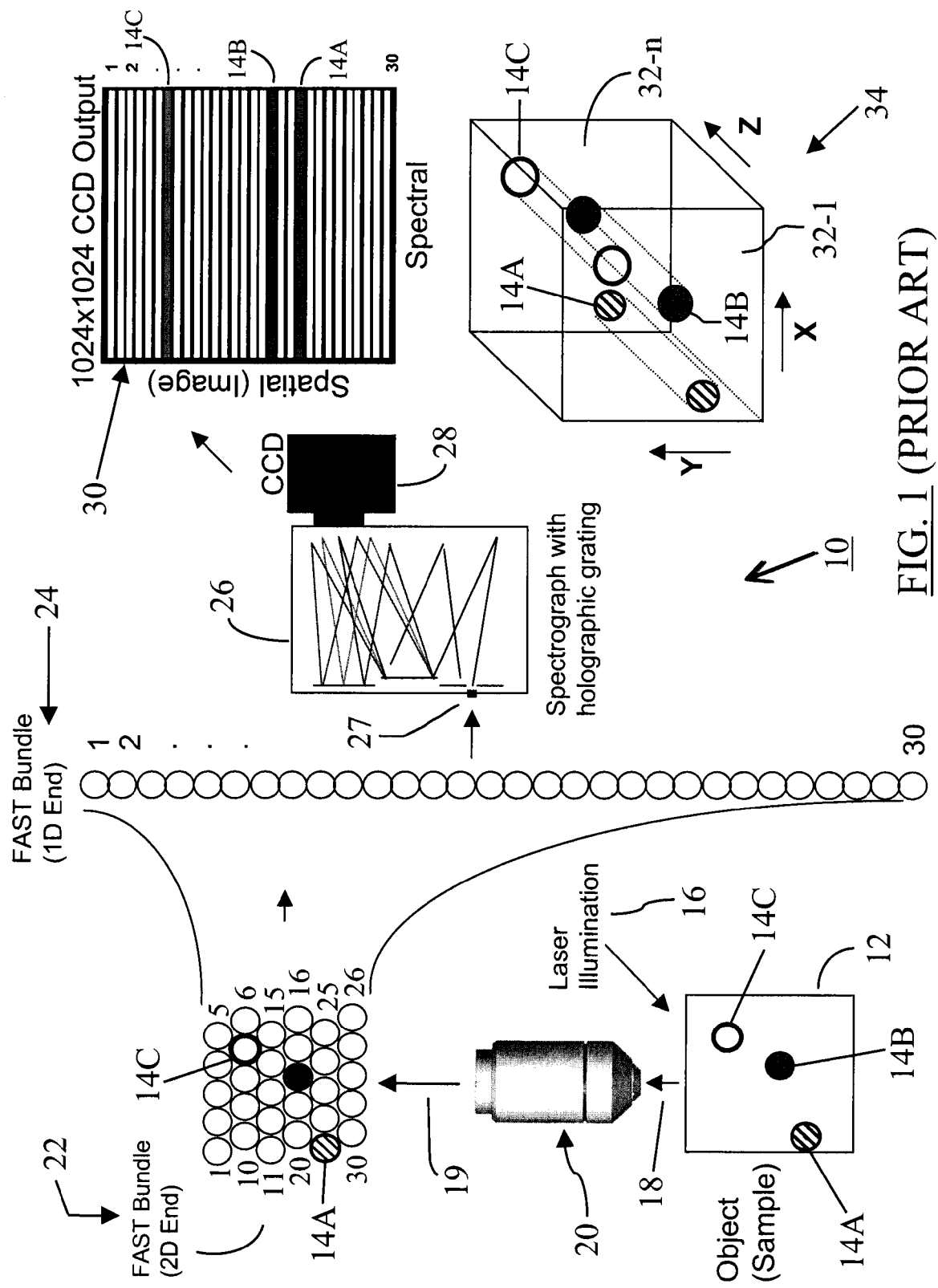
FIG. 1 illustrates a prior art fiber array spectral translator (FAST) based spectroscopy system that may be used for Raman spectroscopy.
Figure 4:
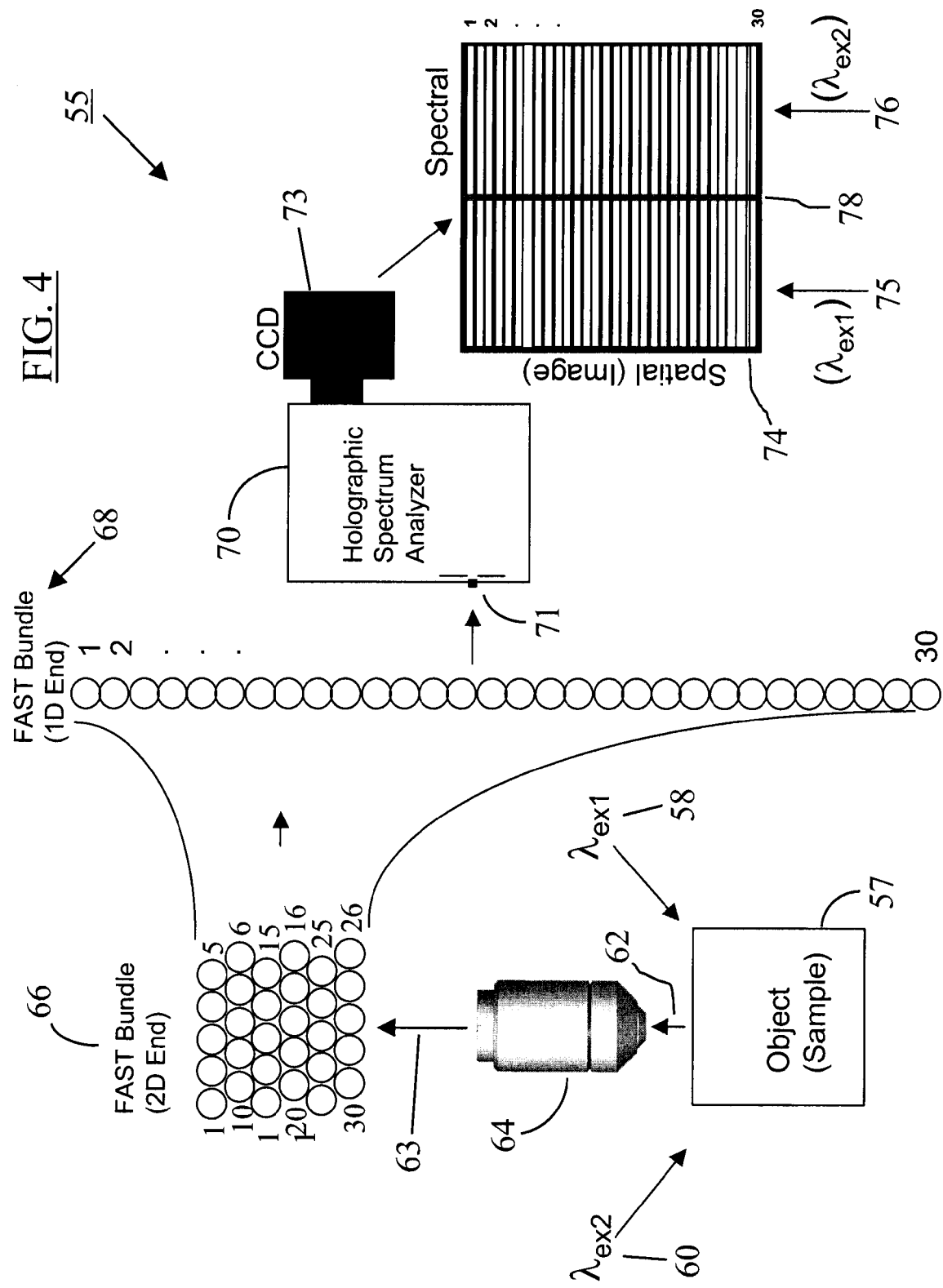
FIG. 4 depicts an exemplary FAST based Raman spectroscopy system according to one embodiment of the present disclosure that is configured to accommodate two illumination light sources and collect spectral portions of interest from both light sources using a single detector in conjunction with a spectral analysis system.

FIG. 4 depicts an exemplary FAST based Raman spectroscopy system 55 according to one embodiment of the present disclosure that is configured to accommodate two illumination light sources 58, 60 and collect spectral portions of interest from both light sources using a single detector 73 in conjunction with a spectral analysis system. In one embodiment, the spectral analysis system includes a holographic spectrum analyzer 70. It is noted that in the system 10 of FIG. 1, after the illumination of the FOV, the optical material information will be collected by a fiber bundle and spectrally resolved through the spectrograph 26 and visualized through a 2D CCD detector 28. However, in contrast with the system 10 in FIG. 1, the system 55 in FIG. 4 employs two excitation sources 58, 60 and uses a holographic spectrum analyzer (HSA) 70 as a spectrograph so as to enable splitting of the spectrally resolved information of the entire illuminated sample FOV into more than one interested region as discussed in more detail below. The result of the customized split can be a higher spectral resolution of the spectral region of interest that results in more detailed material information.

The system 55 may be implemented as part of an imaging spectroscopy apparatus (e.g., a spectral imaging microscope, a Raman chemical or molecular imaging system, a chemical imaging spectrometer, etc.). Similarly, the systems illustrated in FIGS. 6 and 7 (and discussed later hereinbelow) may also be implemented as part of such spectroscopy apparatuses.

Although the discussion below focuses on Raman spectroscopy, the system 55 may be used in various other spectroscopy applications including, for example, fluorescence spectroscopy, NIR (near infrared) spectroscopy, etc. Depending on the desired spectroscopy application, suitable excitation sources 58, 60 may be selected as is known to one skilled in the art. In one embodiment, the illumination sources 58, 60 may provide monochromatic excitation of specific wavelengths $\lambda_{ex1}$ and $\lambda_{ex2}$, respectively. In one embodiment, $\lambda_{ex2} > \lambda_{ex1}$. The illumination sources 58, 60 may provide illuminating photons with wavelengths selected from the wavelengths in the ultraviolet (UV) region, visible light region, or the infrared (including NIR and far infrared) region of the electromagnetic spectrum. In one embodiment, from the visible wavelength lasers, a green laser may be selected for the lower excitation wavelength (e.g., $\zeta_{ex1}$=532 nm or 488 nm), whereas a red laser may be selected for the higher excitation wavelength (e.g., $\lambda_{ex2}$=635 nm or 647 nm). Furthermore, depending on the desired spectroscopy application, suitable illumination or excitation sources may include, for example, lasers, UV LEDs (light emitting diodes), etc.

In the embodiment of FIG. 4, a sample (or object under investigation) 57 is shown to obliquely receive illuminating photons from two different illumination sources 58, 60. However, in one embodiment, a single illumination source (not shown) capable of providing two or more different excitation wavelengths may also be used. Furthermore, a non-oblique illumination (e.g., vertical illumination) may also be implemented as per system design. Some exemplary samples may includes chemical or biological substances, hazardous materials, bio-chemical materials or objects, etc. Photons reflected, emitted, or scattered from the sample 57 in response to the sample's reception of illuminating photons from one or more excitation sources 58, 60 may be collected by collection optics in the system 55. An exemplary photon collection path is indicated by directional arrows 62 and 63 in the embodiment of FIG. 4. In one embodiment, photon collection optics may include a lens unit 64 and a FAST fiber bundle having a 2D end 66 and a curvilinear (1D) end 68 as shown by way of illustration in FIG. 4. The lens unit 64 may include one or more optical lenses (e.g., lens assembly of a microscope objective) providing photons collected from the illuminated sample 57 to the 2D array 66 of the fiber bundle. As in the system 10 of FIG. 1, the fiber bundle of the FAST system acts as a conduit of optical signals received from the sample 57. As in the embodiment of FIG. 1, the fiber bundle in the system 55 is shown to be comprised of thirty (30) exemplary fibers arranged in a 2D array 66 proximate to the lens unit 64. The total number of fibers may be different (e.g., more or less than the 30 fibers shown in FIG. 4) in other embodiments. The optical signals received by the 2D array of optical fibers 66 are fed to an entrance slit 71 of the holographic spectrum analyzer 70 via the curvilinear (1D) end 68 of the FAST fiber bundle. Thus, the photon collection optics may provide the received photons to the spectral analysis system to obtain, for example, a spectrum of the sample under investigation to analyze the sample content in more detail. As noted before, in the embodiment of FIG. 4, the spectral analysis system includes a gratings-based dispersive spectrograph in the form of the holographic spectrum analyzer (HSA) 70.

It is noted here that in the discussion herein the terms "illumination," "illuminating," and "excitation" are used interchangeably as can be evident from the context. For example, the terms "illumination source" and "excitation source" are used interchangeably. Similarly, the terms "illuminating photons" and "excitation photons" are also used interchangeably. Furthermore, as noted before, although the discussion provided herein is in the context of Raman spectroscopy, various systems described herein may be used for Raman and/or fluorescence spectroscopy or other different spectroscopy applications as desired. Additionally, the terms "optical signal" and "optical data" may be used interchangeably, and the terms "spectral signal" and "spectral data" may also be used interchangeably. The terms "optical data" and "spectral data" sometimes may be used interchangeably because of the essentially optical nature of information collected and processed in the system 55 (and also in systems in FIGS. 6 and 7). However, it is understood that, for ease of discussion, the term "optical data" may be used to refer to those optical information containing signals that are not yet processed by the HSA 70. Optical signals processed by the HSA 70 may be referred to as "spectral data." However, as noted before, the distinction between the terms "optical data" and "spectral data" is not a rigid one and the interchangeable use of these terms is equally contemplated and made clear from the context of discussion herein.

Referring again to FIG. 4, the spectral data-containing signals received at the slit 71 of the HSA 70 are dispersed by the spectrometer gratings (not shown) to provide wavelength-specific spectral content of the photons received from the illuminated sample 57. The HSA 70 may provide spectral data to the optical detector 73 for further processing and display as discussed below. In one embodiment, the detector 73 is a 2D CCD array with 1024×1024 pixel resolution. However, a CMOS (complementary metal oxide semiconductor) or other similar imaging device (not shown) may be used instead of the CCD as desired. In comparison with the embodiment in FIG. 1, the embodiment in FIG. 4 includes an additional light source (i.e., two light sources 58, 60 of different wavelengths, $\lambda_{ex1}$ and $\lambda_{ex2}$). In one embodiment, the light sources 58, 60 are monochromatic lasers, wherein $\lambda_{ex2} > \lambda_{ex1}$. The holographic spectrum analyzer 70 may be configured to focus on spectral portions of interest as discussed below.

Figure 2:
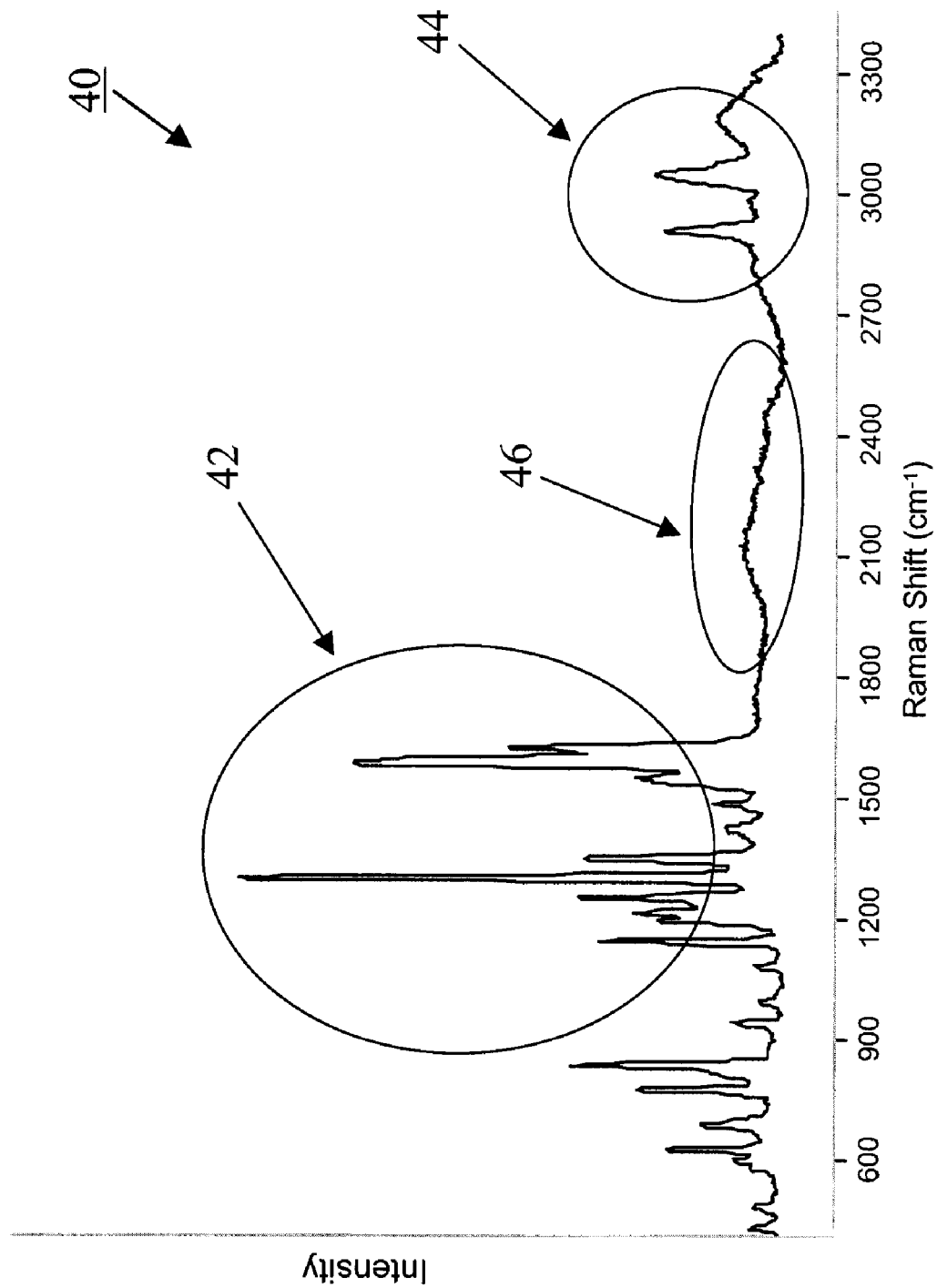
FIG. 2 depicts an exemplary Raman spectrum collected from a sample by one of the fibers in the FAST system of FIG. 1.

In one embodiment, the holographic spectrum analyzer 70 may be constructed according to the teachings of U.S. Pat. No. 6,839,136 (the '136 patent), the disclosure of which is incorporated herein by reference in its entirety. As discussed in the '136 patent, the HSA 70 may separate wavelength information spectrally to allow for focusing on desired portion of the entire spectrum. For example, in an application of the HSA 70 to a Raman spectrum (e.g., the Raman spectrum 40 in FIG. 2) from a single illumination source (e.g., when the sample 57 is illuminated by only one of the excitation sources 58 or 60 in FIG. 4), if the fingerprint region (e.g., the region 42 in FIG. 2) near a laser line is to be focused instead of the C-H stretch region (e.g., the region 44 in FIG. 2) or the intervening region (e.g., the region 46 in FIG. 2), then the HSA 70 may be properly configured to provide spectral data for only the selected fingerprint portion to the CCD 73 coupled thereto. Additional spectral data associated with other spectral regions may be blocked from the CCD 73. In another embodiment, the HSA 70 may be obtained from Headwall Photonics, Inc., of Fitchburg, Mass., USA.

Furthermore, in case of two different laser excitations (e.g., when the sample 57 is illuminated by each of the two laser excitations 58 and 60 in the system 55 in FIG. 4), it may be desired to focus on fingerprint regions in the corresponding spectra from each excitation wavelength. For example, as mentioned before, in the context of Raman spectra 47 and 49 (from two different excitation wavelengths) in FIG. 3, it may be desirable to more closely focus on the fingerprint regions 48 and 50 alone without any distracting details from other spectral regions. In that event, the HSA 70 may be configured to provide selected focused spectral data obtained from the first illumination wavelength ($\lambda_{ex1}$) to a first portion 75 of the CCD 73 and the other relevant spectral data obtained from the second illumination wavelength ($\lambda_{ex2}$) to a second portion 76 of the CCD 73 as illustrated by an exemplary view of a 2D CCD layout or pixel array 74, wherein storage of such divided content is illustrated by an artificial divider line 78. It is noted here that the divider line 78 is for illustration only. In practice, there may not be any such physical division or splitting of CCD pixels (whether row-wise or column-wise) or divisional marking on the CCD pixel array 74. The division of spectral contents from two different excitation wavelengths may be optically and electronically performed by the HSA 70 without the need for a physical division of the CCD pixel array. The storage pixels (not shown) in the CCD array 74 may be considered to have been split row-wise or column-wise to collect corresponding spectral data from the HSA 70. The HSA 70 may be configured to store appropriate spectral data into corresponding portions of the CCD array 74, which data may be then collected and displayed as discussed below with reference to FIG. 5. The terms "row" or "column" as used herein in the context of a 2D CCD array 74 are for ease of discussion and context of reference only, and should not be construed to rigidly define the CCD pixel geometry in any specific orientations or formats. It is evident that the two CCD portions 75, 76 may together constitute the entire spectral data collection surface 74 of the CCD 73 as can be seen from the exemplary layout 74 in FIG. 4. Furthermore, in one embodiment, the pixels constituting the two CCD portions 75, 76 may be physically non-overlapping.

Hence, as illustrated in FIG. 4, more than one excitation wavelength may be used to collect specific spectrally-resolved material information using the HSA 70 and a single, 2D CCD detector 73. The optical signals containing spectrally-resolved material information from the different excitation wavelengths may be collected in a specific CCD region due to a customizable holographic grating architecture of the HSA 70. For Raman imaging applications, it may be possible to collect scattered light from the illuminated FOV (Raman) of the sample 57 together with emitted light (luminescence). The material-specific Raman information may be identical for both excitation wavelengths. Thus, the spectral information in case of Raman signals from two different excitation wavelengths may be the same except for the spectral resolution; the spectral resolution will be higher with longer wavelength excitation as mentioned earlier. However, the luminescence/fluorescence information may be different for the illuminated FOV of the sample for the different excitation wavelengths. Therefore, the use of more than one excitation wavelength and the customized collection of specific spectrally-resolved optical information (Raman and/or luminescence) with one HSA 70 and a single CCD 73 can allow a user to get material-specific information in a 2D image format with additional environmental information (e.g., the kind and degree of impurities due to the characteristic of the spectrally resolved luminescence information from the sample 57).

In one embodiment, the excitations may be applied sequentially. For example, the sample 57 may be first illuminated with the laser excitation wavelength $\lambda_{ex1}$ and Raman spectral data of the fingerprint region (not shown) collected by the FAST fibers may be focused using the HSA 70 and collected in the appropriate portion 75 of the CCD 73. Thereafter, the sample 57 may be illuminated with the second laser wavelength $\lambda_{ex2}$ and the Raman spectral data of the corresponding fingerprint region (not shown) may be collected in the appropriate portion 76 using the combination of the HSA 70 and CCD 73 as discussed before. During such sequential switching of excitation wavelengths, the gratings (not shown) in the HSA 70 need not be re-aligned. Also, the collection of the spectral data in the second portion 76 may be performed without removing the earlier-collected spectral data in the first portion 75.

In an alternative embodiment, laser excitations 58, 60 may be applied substantially simultaneously to the sample 57. In this embodiment, to prevent interference from optical data from two excitations and for ease of optical illumination and data collection purpose, the sample may be considered as being divided into two non-overlapping sample regions (not shown). The first region (not shown) of the sample 57 may be illuminated with the first excitation wavelength ($\lambda_{ex1}$) whereas the second, non-overlapping region (not shown) of the sample 57 may be simultaneously illuminated with the second excitation wavelength ($\lambda_{ex2}$). It is observed here that all the thirty (30) fibers in the fiber bundle may not receive optical signals from all the regions of the sample in this case. For example, half of the fibers in the 2D bundle 66 may receive optical information from a corresponding region of the sample 57, whereas the other half of the fibers may receive optical data from the other region of the sample when, for example, the sample is considered to be vertically divided into substantially two equal regions (not shown). The optical data received from the illuminated sample regions by corresponding fibers may be then processed through the HSA 70 and CCD 73 combination. However, in such an embodiment, half of the rows in the 2D CCD array 74 may contain spectral data from the corresponding half of the fibers, whereas the other half of the rows may contain spectral data from the remaining half of the fibers. Thus, in this case, the divider line 78 may be considered to be placed horizontally (as opposed to the vertical depiction in FIG. 4) dividing the CCD columns into half. An exemplary illustration of such division is provided by the divider line 99 in FIG. 6, which is discussed later hereinbelow. As noted before, the divider line 78 is for illustration only, and should not be considered as implying any rigid physical, electronic, or optical division of CCD pixel array 74. From the foregoing discussion, it is evident that the combination of the HSA 70 and CCD 73 may be configured to flexibly store spectral data from multiple excitation sources in corresponding portions (row-wise or column-wise) of the 2D CCD array 74.

In one embodiment, the HSA 70 may be electronically controlled in such a manner that, initially, only one excitation (e.g., at wavelength $\lambda_{ex1}$) may be applied and the spectral data from each fiber (from the exemplary fiber bundle of thirty fibers numbered "1" through "30" in FIG. 4) for the entire Raman spectrum may be collected at the CCD 73 using the entire spectral data collection surface 74 of the CCD 73. Thereafter, a user may view an average of the collected spectra (from all fibers) to then focus on a portion of the average spectrum that the user wishes to view in more detail. In that case, if a user wishes to focus more on the fingerprint region, then the sample 57 may be illuminated again with the same excitation wavelength (here, $\lambda_{ex1}$) and HSA 70 may be suitably programmed to provide the spectral data for only the relevant fingerprint region (from the first excitation wavelength) to the appropriate portion (e.g., portion 75) of the CCD 73 for collection and further analysis. In one embodiment, in the absence of data for any other spectral region (from the same or different excitation wavelength), such focused spectral data may be collected by the entire CCD array 74 (i.e., in both of the portions 75 and 76). On the other hand, in case of a second excitation wavelength, the above procedure may be repeated to first enable the user to focus on or select another appropriate spectral region of interest from the second excitation wavelength. Thereafter, the sample 57 may be illuminated again with the same second excitation wavelength (here, $\lambda_{ex2}$) and HSA 70 may be configured to provide the spectral data for only the second selected spectral region (from the second excitation wavelength) for collection in the corresponding CCD portion (e.g., portion 76) without affecting prior collection and storage of the first spectral data in the other CCD portion 75. Thus, spectral data for selected excitation-specific spectral regions of interest may be collected in the 2D CCD pixel array 74 for later simultaneous (juxtaposed) display of corresponding spectral regions as discussed below with reference to FIG. 5.

Figure 5:
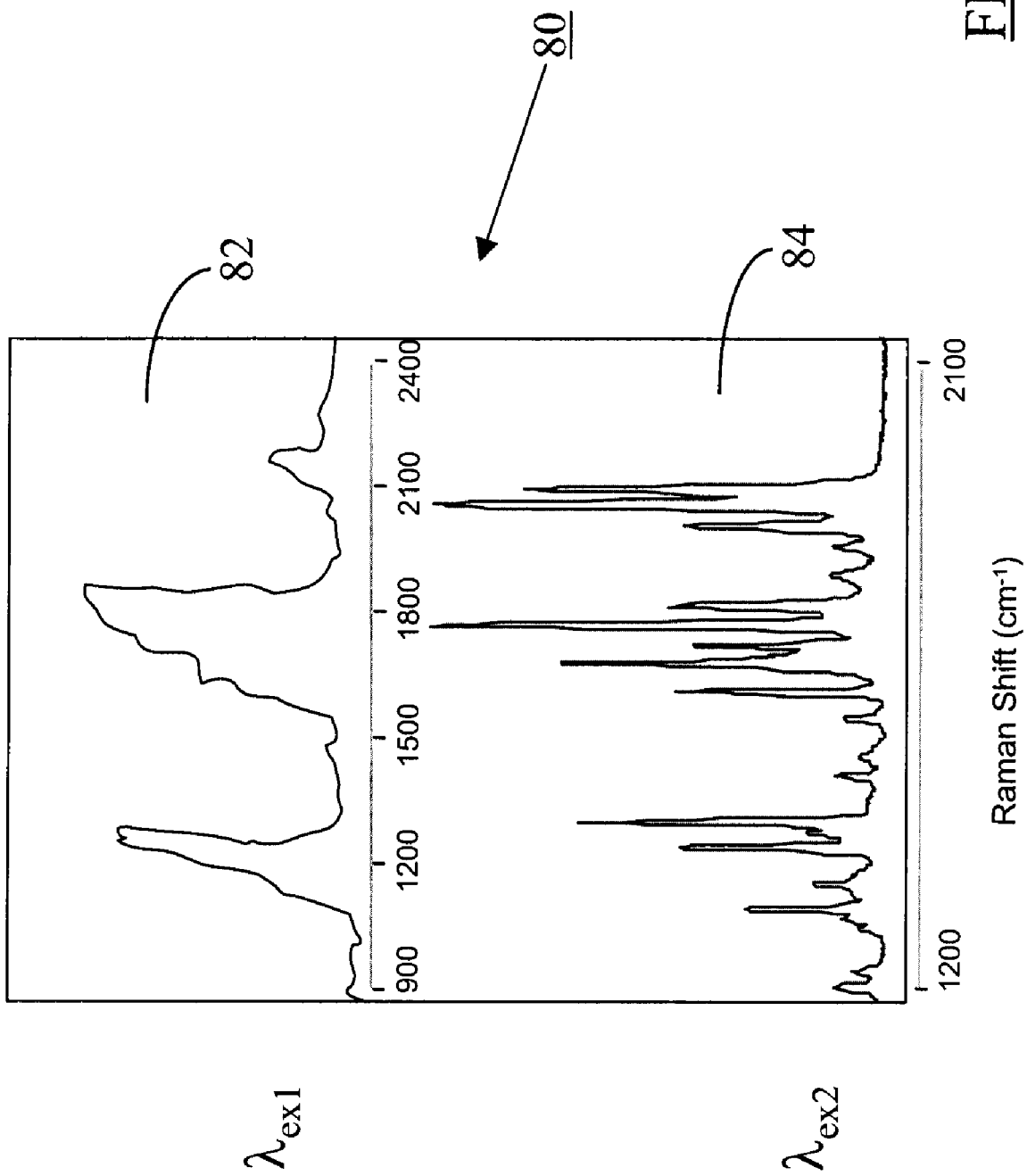
FIG. 5 illustrates an exemplary display of two spectra representing an average of fingerprint portions of corresponding Raman spectra obtained from optical data collected by the fibers in the FAST fiber bundle in the system in FIG. 4 when the sample is illuminated with respective excitation wavelengths $\lambda_{ex1}$ and $\lambda_{ex2}$ (wherein $\lambda_{ex2} > \lambda_{ex1}$)

FIG. 5 illustrates an exemplary display 80 of two spectra 82, 84 representing an average of fingerprint portions of corresponding Raman spectra (e.g., similar to spectra 47 and 49 in FIG. 3) obtained from optical data collected by the fibers in the FAST fiber bundle in the system in FIG. 4 when the sample 57 is illuminated with respective excitation wavelengths $\lambda_{ex1}$ and $\lambda_{ex2}$ (wherein $\lambda_{ex2} > \lambda_{ex1}$) The simultaneous display of two spectral regions 82, 84 may be obtained using the system 55 in FIG. 4 to electronically split the CCD rows into two portions to store separate spectral data therein from the HSA 70 as discussed earlier. The excitation-specific optical data portions can be then processed and displayed in a juxtaposed manner on an electronic display unit or screen (e.g., a liquid crystal display screen or a computer monitor) (not shown) as illustrated in the exemplary display 80 of FIG. 5. It is seen from FIG. 5 that the fingerprint portion 82 associated with a lower excitation wavelength ($\lambda_{ex1}$) has less resolution (but, better free spectral range (FSR)) as compared to the fingerprint portion 84 obtained from a higher excitation wavelength ($\lambda_{ex2}$). As mentioned earlier, the fingerprint portion 82 may be considered an average of corresponding fingerprint regions 50 (FIG. 3), whereas the fingerprint portion 84 may represent an average of corresponding fingerprint regions 48 (FIG. 3). The spectrum from a higher excitation wavelength ($\lambda_{ex2}$) may represent higher spectral groove density, which translates into better resolution. In one embodiment, from the visible wavelength lasers, a green laser may be selected for the lower excitation wavelength (e.g., $\lambda_{ex1}$=532 nm or 488 nm), whereas a red laser may be selected for the higher excitation wavelength (e.g., $\lambda_{ex2}$=635 nm or 647 nm).

It is seen from the exemplary display 80 in FIG. 5 that the X-axis (or horizontal axis) representing Raman shift (in "$cm^{-1}$") may contain different wavenumbers for the different spectral regions of interest. For example, in case of the fingerprint region 82, the Raman shift scale is depicted to contain wavenumbers in the range of 900 to 2400. whereas, the fingerprint region 84 is depicted along a different Raman shift scale from 1200 to 2100 wavenumbers. Thus, because of different spectral resolutions of the fingerprint regions 82, 84, their plots may be depicted along different Raman shift scales without the need to truncate any spectra or conform one spectral scale to the other. In other words, the spectral displays 82, 84 from two different excitation wavelengths may be depicted independently of each other.

In one embodiment, instead of displaying spectra related to a single spectroscopy method (e.g., Raman, fluorescence, NIR, etc.), a combination of spectra obtained from different spectroscopy methods also may be simultaneously displayed using the configuration of HSA 70 and CCD 73 in the system 55 of FIG. 4. For example, the first CCD portion 75 may contain Raman spectral data whereas the second portion 76 may contain fluorescence spectral data, or vice versa. In an alternative embodiment, both CCD portions 75-76 may contain luminescence spectral data as opposed to Raman spectral data as discussed hereinbefore. Different other spectral data storage configurations may be devised using the teachings of the present disclosure.

Figure 6:
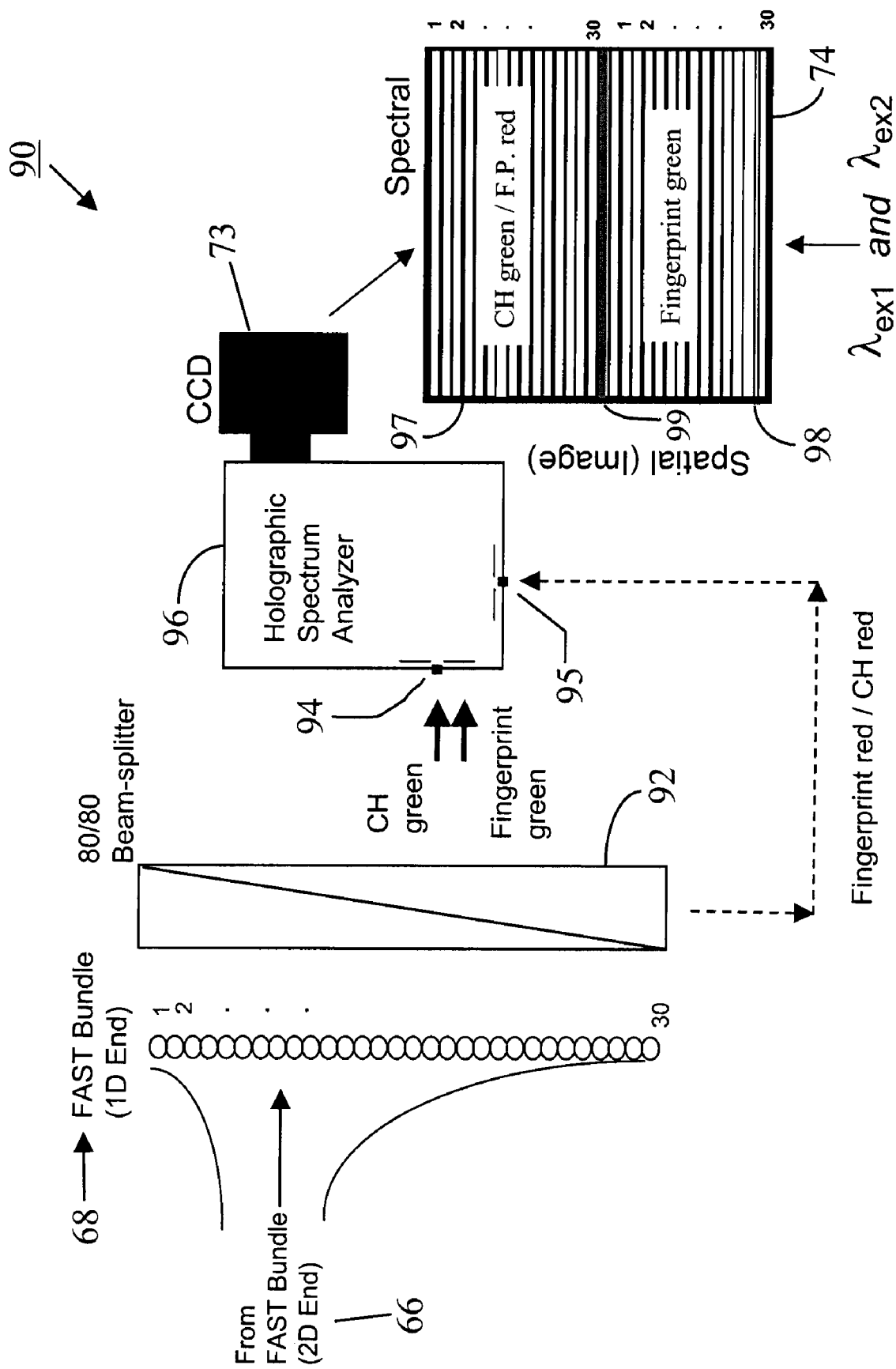
FIG. 6 shows a partial schematic of a modified version of the FAST based Raman spectroscopy system in FIG. 4 according to another embodiment of the present disclosure.

FIG. 6 shows a partial schematic of a modified version of the FAST based Raman spectroscopy system 55 in FIG. 4 according to another embodiment of the present disclosure. Because of substantial similarity between various components in the system 55 (FIG. 4) and the system 90 in FIG. 6, similar reference numerals are used in FIG. 6 for identical or functionally similar components between the systems in FIGS. 4 and 6. Furthermore, discussion of components common between the systems in FIGS. 4 and 6 is not repeated herein for the sake of brevity. Also, for ease of illustration, the two illumination sources 58, 60, the sample 57, the lens unit 64 and 2D FAST fiber bundle 66, are not shown in FIG. 6 even though these components are part of the system 90. It is observed, however, that, in the system 90 in FIG. 6, a different type of holographic spectrum analyzer (HSA) 96 is used in conjunction with an 80/80 beam splitter 92. Depending on the illumination wavelengths (as discussed below), the photons reflected, emitted, or scattered from the sample 57 are transferred to the HSA 96 via different output channels (not shown) of the 80/80 beam splitter 92, instead of a substantially direct transfer from the fiber bundle as in the system 55 in FIG. 4.

As illustrated in FIG. 6, the HSA 96 may include two separate slits 94, 95. In one embodiment, the single slit based HSA 70 may be modified to include two separate slits to selectively receive photons of two different wavelengths (as discussed below with reference to the HSA 96 in FIG. 6). In the embodiment of FIG. 6, columns in the 2D CCD pixel array 74 is shown divided into half by an artificial and exemplary divider line 99. Because of such division, the pixels in the CCD layout 74 may be considered as being partitioned into two portions 97, 98. In one embodiment, the portions 97, 98 may be physically non-overlapping and may together constitute the spectral data collection surface of the CCD 73. The horizontal division (as shown by the exemplary divider line 99 in FIG. 6) of the CCD array 74 may provide better spectral resolution (e.g., along x-axis) than the vertical division (as shown by the exemplary divider line 78 in FIG. 4). On the other hand, the vertical division in FIG. 4 may provide better spatial resolution (e.g., along y-axis) as compared to the horizontal division in FIG. 6. Thus, in the embodiment of FIG. 6, each CCD portion 97, 98 may store spectral data from substantially more individual wavelengths in the spectral region of interest selected by the HSA 96 because of availability of the full spectral range of the CCD 73 (e.g., 1024 pixels along the x-axis) to store data received from each optical fiber. However, there may be less pixels per fiber (i.e., less spatial resolution) along the other dimension (e.g., the spatial dimension or y-axis) of each data collection portion 97, 98. For example, in case of a CCD array 74 with a size of 1024×1024 pixels, there may be 1024/30=34 (approximately) pixels per fiber line in the embodiment of FIG. 4 where spatial resolution (e.g., along y-axis) is shared among thirty (30) fibers. On the other hand, in the embodiment of FIG. 6, the spatial dimension (y-axis) is shown divided between two groups of thirty (30) fibers each. In that event, the spatial resolution per fiber line in the embodiment of FIG. 6 may be approximately half (i.e., 17 pixels) of the spatial resolution in the embodiment of FIG. 4.

In one embodiment, the sample 57 may be sequentially illuminated by a green laser excitation ($\lambda_{ex1}$) 58 followed by a red laser excitation ($\lambda_{ex2}$) or vice versa. In case of sequential excitation, the beam splitter 92 may not split the wavelengths of photons received from the ID fiber bundle 68 because of presence of only one excitation wavelength at a time. However, in case of a simultaneous excitation (e.g., excitation of the sample 57 with both the green and red illumination sources operating in parallel), the beam splitter 92 may be configured to transmit 80% of photons from one excitation wavelength in one direction (e.g., towards the slit 94) and transmit 80% of photons from another excitation wavelength in another direction (e.g., towards the slit 95 as indicated by the dotted path) as discussed later below. The embodiment in FIG. 6 illustrates that when the sample 57 is illuminated just with the green excitation, photons from all 30 fibers and from all spectral regions of interest (e.g., CH-region, fingerprint region, etc.) may be initially received by the HSA 96 via the slit 94. The LISA 96 may be then configured to provide photons from user-selected spectral portions of interest to the CCD 72 for a simultaneous display of selected spectral portions as per the teachings of one embodiment of the present disclosure. In FIG. 6, the spectral data of the CH region from green excitation is shown collected by the CCD portion 97, whereas the spectral data of the fingerprint portion from green excitation is shown collected by the CCD portion 98. These spectral regions of interest may be later displayed simultaneously on a single display screen as discussed hereinbefore. Similarly, in case of just the red excitation (or any other single illumination), spectral data from user-desired spectral regions of interest may be collected in different portions of the CCD array 74.

In case of a sequential excitation (e.g., green excitation followed by red excitation), in one embodiment, the HSA 96 may be configured to first provide spectral data from the green CH and fingerprint regions to portions 97, 98, respectively, as discussed before. Thereafter, upon red excitation, the beam splitter 92 may provide photons from all spectral regions of interest (e.g., CH region, fingerprint region, etc.) to the slit 94. The HSA 96 may be configured to provide photons from one of the user-selected spectral region of interest (e.g., red fingerprint region) to one of the CCD portions 97, 98, thereby replacing the earlier stored spectral data therein. For example, spectral data of red fingerprint region may be stored in the CCD portion 97 replacing earlier-stored spectral data of green CH region. In an alternative embodiment, in case of a sequential illumination, the HSA 96 may provide spectral data for only one spectral region of interest to a corresponding CCD portion (e.g., portion 97 or 98). Thus, for example, the CCD portion 98 may receive the green fingerprint data, whereas the CCD portion 97 may not receive any spectral data when green excitation is provided. Thereafter, when the red excitation is provided, the remaining CCD portion 97 may receive the spectral data of the user-selected spectral region of interest (e.g., the red fingerprint region). Different or alternative storage approaches may be similarly conceived and implemented in case of individual or sequential excitations from two illumination sources.

It is observed here that there may be significant background fluorescence (or noise) in case of Raman spectral data collected for fingerprint region from green excitation. However, in case of higher wavenumbers—e.g., Raman spectral data for the CH region from green excitation or the fingerprint region from red excitation—the Raman spectral data may exhibit less background fluorescence (i.e., stronger signal-to-noise ratio or SNR). In one embodiment, differentiation between the CH and fingerprint regions of green excitation-each region having different SNR-may be visualized using the HSA 96 and the split CCD 73 as discussed above. However, a parallel illumination of the sample 57 with green and red lasers simultaneously may allow for simultaneous collection of spectral data from green and red fingerprint regions so as to enable a user to compare or contrast the two spectral regions (with different levels of fluorescence background noise) from the same sample 57, which may further enable the user to calculate or reconstruct the weak (green) fingerprint spectrum from the stronger (red) fingerprint spectrum juxtaposed therewith. The higher spectral resolution may further allow a more detailed comparison of the selected spectral regions of interest.

As mentioned before, in case of parallel excitations, the beam splitter 92 may split photons associated with green and red excitations in such a manner that green excitation-related photons may be sent to the HSA slit 94 whereas the red excitation-related photons may be substantially simultaneously sent to the HSA slit 95 (as indicated by the exemplary dotted line). In case of simultaneous excitation, as noted before, the HSA 96 may be configured such that it may simultaneously and selectively process optical signals received at its two slits 94, 95, and provide Raman spectral data of green fingerprint region to the CCD portion 98, while substantially simultaneously providing Raman spectral data of red fingerprint region to the CCD portion 97. These simultaneously-collected, user-selected spectral regions of interest may be then jointly displayed on a single display screen as shown, for example, in the exemplary display in FIG. 5. As before, the HSA 96 may block optical signals associated with other, non-selected Raman spectral regions of interest (e.g., the green CH region, or red CH region, etc.) from reaching the CCD detector array 74. Thus, in one embodiment, spectral data of user-selected spectral regions of interest may be simultaneously collected and displayed using a two slit-based HSA 96 in combination with a "split" CCD 73 as discussed herein.

As can be seen from the configuration in FIG. 6, each excitation-specific set of photons may be supplied by all of the fibers in the fiber bundle 68. Therefore, each portion 97, 98 of the CCD array 74 may receive corresponding excitation-specific photons collected from the illuminated sample 57 by all the thirty (30) fibers, albeit at a reduced spatial resolution as discussed hereinbefore. Therefore, although the CCD layout 74 depicts two sets of thirty (30) fibers—each set of thirty (30) fibers shown associated with a corresponding one of the CCD portions 97, 98—it is evident from the discussion here that the CCD portion-specific sets of fibers are for illustration purpose only. Actually, in the system 90 in FIG. 6, there may be only one physical set of thirty optical fibers in the fiber bundle to receive photons reflected, emitted, or scattered from the sample 57 when the sample 57 is simultaneously illuminated by two different excitation wavelengths.

Figure 7:
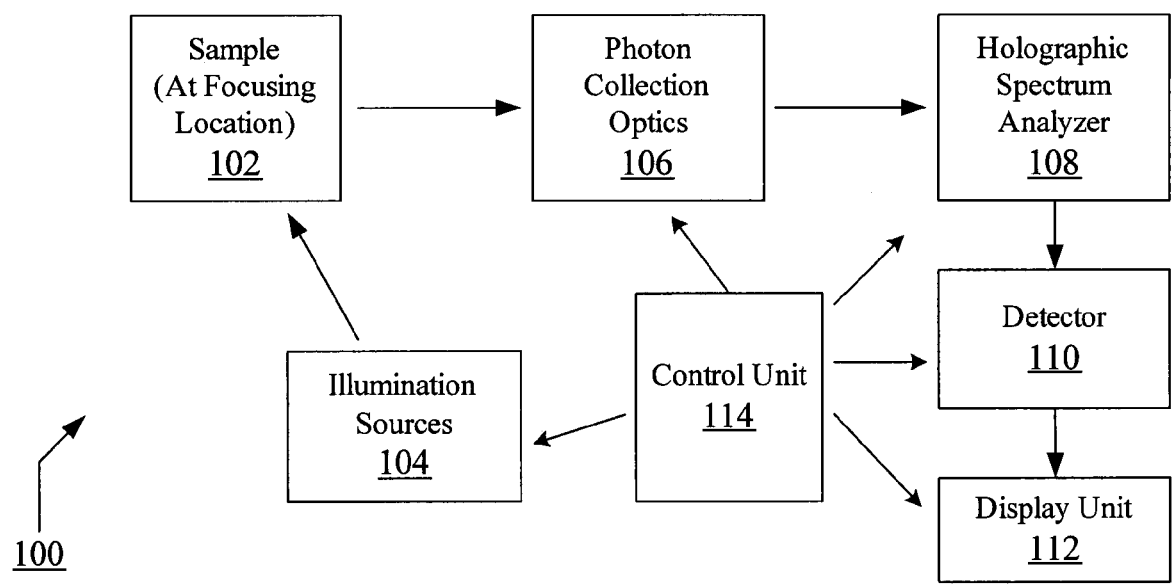
FIG. 7 illustrates a block diagram of an exemplary Raman and/or fluorescence spectroscopy system according to one embodiment of the present disclosure.

FIG. 7 illustrates a block diagram of an exemplary Raman and/or fluorescence spectroscopy system 100 according to one embodiment of the present disclosure. The system 100 may be a dual-excitation, FAST-based spectroscopy unit with a single detector (e.g., one of the systems shown in FIGS. 4 and 6) as per the teachings of the present disclosure. The system 100 may include multiple illumination sources 102 (e.g., laser diodes, or LEDs) that directly provide illuminating photons to a sample 104. The sample 104 may be placed on a receptacle (not shown) that is a part of the system 100. Alternatively, an assembly including the sample 104 and its receptacle may be placed within the system 100 whenever needed during operation of the system 100. In one embodiment, there are two illumination sources in the system 100 providing photons of different excitation wavelengths as in the case of embodiments in FIGS. 4 and 6. The sample 104 may interact with the illuminating photons to provide reflected, scattered, or emitted photons, which photons may be initially collected by the photon collection optics 106 and transferred to a spectral analysis unit 108. In one embodiment, the photon collection optics 106 may include a lens assembly either alone or in combination with a laser line rejection filter (not shown). The photon collection optics 106 may also include a FAST (fiber array spectral translator) fiber bundle optically coupled to the lens assembly as illustrated, for example, in the embodiments of FIGS. 4 and 6.

The photon collection optics 106 may direct all or a portion of the Raman scattered or fluorescence (emitted) photons received from the sample to the spectral analysis unit 108, which may be a dispersive (e.g., gratings-based) holographic spectrum analyzer (HSA) as shown in the exemplary embodiments of FIGS. 4 and 6. As discussed hereinbefore, for each illumination wavelength, the HSA 108 may measure a spectrum of the sample 104 under investigation and may be configured to select an excitation-specific spectral region of interest (e.g., a fingerprint region) and provide photons associated only with the selected spectral region of interest to an optical detector 110. As in the embodiments of FIGS. 4 and 6, the optical detector 10 may be a CCD (charge coupled device) array. Alternatively, the detector 110 may include a CMOS (complementary metal oxide semiconductor) array. The detector 10 may be configured to generate data that can be used to display spectral images of the sample 104. The detector 110 may detect photons associated with selected spectral regions of interest (e.g., a wavelength-dispersed optical signal) and received from HSA 108. The CCD pixels in the detector 110 may thus collect spectral data associated with selected spectral regions of interest and the detector 110 may then generate signal data therefrom. The signal data may be supplied to an electronic display unit 112 to provide a simultaneous display of selected spectral regions of interest as shown, for example, in FIG. 5. In one embodiment, the display unit 112 may be a computer display screen, a display monitor, or an LCD (liquid crystal display) screen. Thus, as discussed hereinbefore in more detail with reference to discussion of FIGS. 4 and 6, the spectroscopy system 100 may use two illumination sources in combination with a single CCD 110 and the HSA 108 to provide simultaneous displays of selected spectral regions of interest. The spectroscopy system 100 may be implemented in the form of a desktop unit or a compact, mobile spectroscopy unit (e.g., for portable or handheld spectroscopy applications).

The spectroscopy system 100 may also include a programmable control unit 114, which can be suitably programmed to electronically control functionalities of one or more of the system elements including, for example, each illumination source in the group of illumination sources 102, the collection optics 106, the spectral analysis unit 108, the detector 110, and the display unit 112 as shown by the exemplary illustration in FIG. 7. The control unit 114 may be a computing or data processing unit that can be suitably programmed for collecting and processing spectral information from the samples under investigation.

The foregoing describes various embodiments of a single detector based spectroscopy system using FAST (fiber array spectral translator) fibers and two excitation sources in conjunction with a holographic spectrum analyzer (HSA) to obtain simultaneous and selective display of spectroscopic regions of interest. A sample can be illuminated with different laser excitation wavelengths and resulting multiple spectra can be comparatively observed on a single display screen for more fruitful analysis of sample spectral responses (and, hence, sample chemical or physical properties) under different excitations. The HSA may be configured to focus on user-selected spectral regions of interest from different such spectra and a single CCD detector may be configured to collect spectral data from all selected spectral regions of interest in corresponding portions of the CCD pixel array, thereby allowing subsequent simultaneous display of such selected spectral regions of interest. Instead of portions of different spectra (from different excitation wavelengths), the HSA may also allow simultaneous collection and display of portions of a single spectrum from a single excitation wavelength. A user can perform better comparative analysis when spectral regions of interest are juxtaposed with each other on a single electronic display.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method comprising:
    illuminating a sample with first photons having a first excitation wavelength;
    collecting first spectral data from second photons reflected, scattered, or emitted from said sample when said sample is illuminated with said first photons, wherein said first spectral data are collected using a first portion of an optical detector;
    illuminating said sample with third photons having a second excitation wavelength, wherein said second excitation wavelength is different from said first excitation wavelength; and
    collecting second spectral data from fourth photons reflected, scattered, or emitted from said sample when said sample is illuminated with said third photons, wherein said second spectral data are collected using a second portion of said optical detector without removing said first spectral data collected by said first portion.

2. The method of claim 1, wherein said first and said second portions of said optical detector are different, and wherein said first and said second portions together constitute the entire spectral data collection surface of said optical detector.

3. The method of claim 1, wherein said second excitation wavelength is higher than said first excitation wavelength.

4. The method of claim 1, wherein each of said first and said second excitation wavelengths is selected from one of the following: an NIR (near infrared) wavelength range, a visible wavelength range, and a UV (ultraviolet) wavelength range.

5. The method of claim 4, wherein said first excitation wavelength is 532 nm or 488 nm, and wherein said second excitation wavelength is 635 nm or 647 nm.

6. The method of claim 1, wherein collecting said first spectral data includes:
    receiving a portion of said second photons at a holographic spectrum analyzer;
    configuring said holographic spectrum analyzer to measure a first spectrum of said sample using said portion of said second photons;
    further configuring said holographic spectrum analyzer to select a first spectral region from said first spectrum and supply photons associated only with said first spectral region to said first portion of said optical detector; and
    configuring said first portion of said optical detector to detect photons associated with said first spectral region and collect said first spectral data from said detected photons associated with said first spectral region.

7. The method of claim 6, wherein collecting said second spectral data includes:
    receiving a portion of said fourth photons at said holographic spectrum analyzer;
    configuring said holographic spectrum analyzer to measure a second spectrum of said sample using said portion of said fourth photons;
    further configuring said holographic spectrum analyzer to select a second spectral region from said second spectrum and supply photons associated only with said second spectral region to said second portion of said optical detector; and configuring said second portion of said optical detector to detect photons associated with said second spectral region and collect said second spectral data from said detected photons associated with said second spectral region.

8. The method of claim 7, wherein wavenumbers associated with said first and said second spectral regions are different.

9. The method of claim 1, wherein the steps of illuminating said sample with said first photons and said third photons include one of the following:
   illuminating said sample with said first photons substantially simultaneously with illuminating said sample with said third photons; and
   sequentially illuminating said sample with said first photons and said third photons.

10. The method of claim 9, wherein said substantial simultaneous illumination includes:
    illuminating a first region of said sample with said first photons; and
    substantially simultaneously illuminating a second region of said sample with said third photons, wherein said first and said second regions are different.

11. The method of claim 1, wherein one of the following applies:
    said first spectral data represent Raman spectral data of said sample illuminated with said first photons and said second spectral data represent Raman spectral data of said sample illuminated with said third photons;
    said first spectral data represent luminescence spectral data of said sample illuminated with said first photons and said second spectral data represent luminescence spectral data of said sample illuminated with said third photons;
    said first spectral data represent Raman spectral data of said sample illuminated with said first photons and said second spectral data represent luminescence spectral data of said sample illuminated with said third photons; and
    said first spectral data represent luminescence spectral data of said sample illuminated with said first photons and said second spectral data represent Raman spectral data of said sample illuminated with said third photons.

12. The method of claim 1, further comprising:
    displaying a first spectrum of said sample on a first portion of a display screen using said first spectral data; and
    simultaneously displaying a second spectrum of said sample on a second portion of said display screen using said second spectral data.

13. The method of claim 1, wherein the optical detector is one of the following: a charged coupled device (CCD), and a complementary metal oxide semiconductor (CMOS) array.

14. A method comprising:
    displaying a first spectrum of a sample obtained when said sample is illuminated with first photons having a first excitation wavelength;
    displaying a second spectrum of said sample obtained when said sample is illuminated with second photons having a second excitation wavelength, wherein said second excitation wavelength is different from said first excitation wavelength;
    allowing a user to select a first spectral region of said first spectrum and a second spectral region of said second spectrum; and
    performing the following in response to selection of said first and said second spectral regions by said user:
    illuminating said sample with said first photons;
    configuring a holographic spectrum analyzer to perform the following:
    receive a portion of third photons reflected, scattered, or emitted from the sample when the sample is illuminated with said first photons, and
    supply those of said third photons that are associated with only said first spectral region to a first portion of an optical detector;
    illuminating said sample with said second photons; and
    configuring said holographic spectrum analyzer to further perform the following:
    receive a portion of fourth photons reflected, scattered, or emitted from the sample when the sample is illuminated with said second photons, and
    supply those of said fourth photons that are associated with only said second spectral region to a second portion of said optical detector, wherein said first and said second portions of said optical detector are different, and wherein said first and said second portions together constitute the entire spectral data collection surface of said optical detector.

15. The method of claim 14, further comprising:
    configuring said optical detector to detect photons associated with only said first spectral region to generate a first spectral data therefrom;
    configuring said optical detector to detect photons associated with only said second spectral region to generate a second spectral data therefrom; and
    further configuring said optical detector to provide said first and said second spectral data to facilitate simultaneous display thereof.

16. The method of claim 15, further comprising:
    displaying a first spectrum of said sample on a first portion of a display screen using said first spectral data; and
    simultaneously displaying a second spectrum of said sample on a second portion of said display screen using said second spectral data.

17. A system comprising:
    a first illumination source for illuminating a sample with first photons having a first excitation wavelength;
    an optical detector having a first portion and a second portion that together constitute the entire spectral data collection surface of said optical detector, wherein said first portion is different from said second portion, and wherein said first portion of said optical detector is configured to collect first spectral data from second photons reflected, scattered, or emitted from said sample when said sample is illuminated with said first photons;
    a second illumination source for illuminating said sample with third photons having a second excitation wavelength, wherein said second excitation wavelength is different from said first excitation wavelength; and
    said second portion of said optical detector that is configured to collect second spectral data from fourth photons reflected, scattered, or emitted from said sample when said sample is illuminated with said third photons, wherein said optical detector is configured to collect said second spectral data without removing said first spectral data collected by said first portion.

18. The system of claim 17, wherein each of said first and said second illumination sources is selected from the group consisting of a laser, and a UV LED (Ultraviolet Light Emitting Diode).

19. The system of claim 17, wherein said second excitation wavelength is higher than said first excitation wavelength, and wherein each of said first and said second excitation wavelengths is selected from one of the following: an NIR (near infrared) wavelength range, a visible wavelength range, and a UV (ultraviolet) wavelength range.

20. The system of claim 17, further comprising:
a collection optics to collect said second photons and said fourth photons;
a spectral analysis system coupled to said collection optics and configured to perform the following:
receive a portion of said second photons and to responsively measure a first spectrum of said sample using said portion of said second photons,
select a first spectral region from said first spectrum and supply photons associated only with said first spectral region to said first portion of said optical detector,
receive a portion of said fourth photons and to responsively measure a second spectrum of said sample using said portion of said fourth photons, and
select a second spectral region from said second spectrum and supply photons associated only with said second spectral region to said second portion of said optical detector;
said first portion of said optical detector configured to detect photons associated with said first spectral region and collect said first spectral data from said detected photons associated with said first spectral region; and
said second portion of said optical detector configured to detect photons associated with said second spectral region and collect said second spectral data from said detected photons associated with said second spectral region.

21. The system of claim 20, wherein said spectral analysis system includes a holographic spectrum analyzer.

22. The system of claim 21, wherein said holographic spectrum analyzer includes:
a first slit configured to receive said portion of said second photons; and
a second slit configured to receive said portion of said fourth photons.

23. The system of claim 22, wherein said second slit is configured to receive said portion of said fourth photons substantially simultaneously with reception of said portion of said second photons by said first slit.

24. The system of claim 22, further comprising:
a beam splitter placed between said collection optics and said holographic spectrum analyzer to receive said second photons and said fourth photons from said collection optics, and to provide said portion of said second photons to said first slit and said portion of said fourth photons to said second slit.

25. The system of claim 20, wherein said collection optics includes.
a lens unit optically coupled to said sample to receive said second and said fourth photons therefrom; and
a fiber array spectral translator (FAST) unit having a first end and a second end, wherein said first end is formed of a plurality of optical fibers arranged in a two dimensional (2D) array and said second end is formed of said plurality of optical fibers arranged in a curvilinear array, wherein said first end of said FAST unit is optically coupled to said lens unit to receive portions of said second and said fourth photons therefrom, and wherein said second end of said FAST unit is optically coupled to said spectral analysis system to transfer said portions of said second and said fourth photons received by said first end to said spectral analysis system.

26. The system of claim 20, further comprising:
a display unit configured to simultaneously display a third spectrum of said sample on a first portion of a display screen using said first spectral data and a fourth spectrum of said sample on a second portion of said display screen using said second spectral data.

27. The system of claim 26, further comprising:
a programmable control unit, which, upon being programmed, is configured to control operations of one or more of the following:
said first illumination source; said second illumination source; said collection optics; said spectral analysis system; said optical detector; and said display unit.

28. The system of claim 17, wherein the optical detector is one of the following: a charged coupled device (CCD), and a complementary metal oxide semiconductor (CMOS) array.

* * * * *